United States Patent
Lam et al.

(10) Patent No.: US 10,234,466 B2
(45) Date of Patent: Mar. 19, 2019

(54) KITS AND METHODS FOR DETERMINING PHYSIOLOGIC LEVEL(S) AND/OR RANGE(S) OF HEMOGLOBIN AND/OR DISEASE STATE

(71) Applicants: EMORY UNIVERSITY, Atlanta, GA (US); THE UNITED STATES OF AMERICA REPRESENTED BY THE SECT OF THE DEPT OF HEALTH AND HUMAN SCVS/CENTERS FOR DISEASE CONTROL, Washington, DC (US); CHILDREN'S HEALTHCARE OF ATLANTA, INC., Atlanta, GA (US); GEORGIA TECH RESEARCH CORPORATION, Atlanta, GA (US)

(72) Inventors: Wilbur A. Lam, Decatur, GA (US); Morgan Byrd, Memphis, TN (US); Erika Tyburski, Decatur, GA (US); Michael L. McKinnon, Decatur, GA (US); Siobhan O'Connor, Decatur, GA (US); Nathan A. Hotaling, Ocala, FL (US)

(*) Notice: Subject to any disclaimer, the term of this patent is extended or adjusted under 35 U.S.C. 154(b) by 900 days.

(21) Appl. No.: 14/411,420

(22) PCT Filed: Mar. 15, 2013

(86) PCT No.: PCT/US2013/032007
§ 371 (c)(1),
(2) Date: Dec. 26, 2014

(87) PCT Pub. No.: WO2014/025401
PCT Pub. Date: Feb. 13, 2014

(65) Prior Publication Data
US 2015/0140670 A1  May 21, 2015

Related U.S. Application Data

(60) Provisional application No. 61/681,242, filed on Aug. 9, 2012.

(51) Int. Cl.
*A61B 5/15* (2006.01)
*A61B 5/151* (2006.01)
(Continued)

(52) U.S. Cl.
CPC ..... *G01N 33/721* (2013.01); *A61B 5/150022* (2013.01); *A61B 5/15105* (2013.01);
(Continued)

(58) Field of Classification Search
CPC ........ A61B 5/150022; A61B 5/150412; A61B 5/15105; A61B 5/157; A61B 5/150343;
(Continued)

(56) References Cited

U.S. PATENT DOCUMENTS

| 3,676,076 A | 7/1972 | Grady |
| 5,541,057 A * | 7/1996 | Bogart ................. G01N 21/21 356/369 |

(Continued)

FOREIGN PATENT DOCUMENTS

| CA | 2891513 | 6/2014 |
| EP | 2676606 | 12/2013 |

(Continued)

OTHER PUBLICATIONS

Office Action issued in Japanese Application No. 2015-526525, dated Jan. 24, 2017, 7 pages.
(Continued)

*Primary Examiner* — Rebecca M Fritchman
(74) *Attorney, Agent, or Firm* — Meunier Carlin & Curfman LLC

(57) ABSTRACT

Diagnostic kits and methods configured to rapidly and non-invasively determine physiologic levels of hemoglobin. A diagnostic kit may include a chamber pre-filled with an indicator, the indicator solution including a tetramethylbenzidine (TMB) solution, the indicator being configured to change color; a collection device configured to collect a test sample from a subject. The kit may also include a hemo-
(Continued)

globin physiologic level identifier legend, the legend indicating 1) at least one color of the indicator and 2) a physiologic level and/or range of the hemoglobin and/or disease state associated with the color.

4 Claims, 9 Drawing Sheets

(51) Int. Cl.
    *A61B 5/157*     (2006.01)
    *G01N 33/72*     (2006.01)

(52) U.S. Cl.
    CPC .. *A61B 5/150305* (2013.01); *A61B 5/150343* (2013.01); *A61B 5/150351* (2013.01); *A61B 5/150358* (2013.01); *A61B 5/150412* (2013.01); *A61B 5/150503* (2013.01); *A61B 5/150755* (2013.01); *A61B 5/157* (2013.01); *G01N 2800/22* (2013.01)

(58) Field of Classification Search
    CPC ........ A61B 5/150351; A61B 5/150358; A61B 5/150503; A61B 5/150755; A61B 5/150305; G01N 33/721; G01N 2800/22
    USPC ............................................ 436/66; 422/419
    See application file for complete search history.

(56) References Cited

U.S. PATENT DOCUMENTS

| | | | |
|---|---|---|---|
| 5,965,453 | A | 12/1999 | Skiffington et al. |
| 2003/0064526 | A1 | 4/2003 | Niedbala et al. |
| 2009/0263905 | A1* | 10/2009 | Scheuringer ........... G01N 33/72 436/66 |
| 2013/0052675 | A1* | 2/2013 | Karlsson ............ A61B 5/14546 435/15 |
| 2014/0072189 | A1 | 3/2014 | Sidhant et al. |
| 2017/0276690 | A1 | 9/2017 | Lam et al. |

FOREIGN PATENT DOCUMENTS

| | | |
|---|---|---|
| JP | 04-067405 | 10/1990 |
| JP | 04-173098 | 6/1992 |
| JP | H09133671 A | 5/1997 |
| WO | 201010881 | 12/2010 |
| WO | 2011040874 A1 | 4/2011 |
| WO | 2013162631 | 10/2013 |
| WO | 2014025401 | 2/2014 |

OTHER PUBLICATIONS

Liem H.H. et al., Quantitative Determination of Hemoglobin and Cytochemical Staining for Peroxidase Using 3,3', 5,5'-Tetramethylbenzidine Dihydrochloride, A Safe Substitute for Benzidine. Analyticalbiochemistry 98, 33-393 (1979) Abstract.
Standefer J.C. et al., Use of Tetramethylbenzidine in Plasma Hemoglobin Assay, Clin. chem. 23/4, 749-751 (1977) Abstract.
Levinson Stanley S., Measuring Hemoglobin in Plasma by Reaction with Tetramethylbenzidine, Clin. chem. 28/3, 471-474 (1982).
International Search Report and Written Opinion issued in International Application No. PCT/US2013/032007, dated Jul. 30, 2013, 5 pages.
International Preliminary Report on Patentability issued in International Application No. PCT/US2013/032007, dated Feb. 10, 2015, 3 pages.
Communication Pursuant to Article 94(3) EPC, issued in European Application No. 13827737.1, dated Nov. 14, 2017, 6 pages.
Search Report issued in European Application No. 13827737.1, dated Mar. 7, 2016, 6 pages.
Second Office Action issued in Japanese Application No. 2015-526525, dated Jan. 9, 2018, 3 pages.
Extended European Search Report issued in EP Application No. 15832416.0, dated Feb. 13, 2018.
International Search Report and Written opinion conducted in International Application No. PCT/US2015/045207, dated Dec. 7, 2015.
International Preliminary Report on Patentability issued in International Application No. PCT/US2015/045207, dated Feb. 14, 2017.
Communication Pursuant to Article 94(3) EPC, issued in European Application No. 13827737.1, dated Apr. 6, 2018, 6 pages.

\* cited by examiner

810

KITS AND METHODS FOR DETERMINING PHYSIOLOGIC LEVEL(S) AND/OR RANGE(S) OF HEMOGLOBIN AND/OR DISEASE STATE

CROSS REFERENCE TO RELATED APPLICATION

This application claims priority to U.S. Provisional Application Ser. No. 61/681,242 filed on Aug. 9, 2012, which is hereby incorporated by this reference in its entirety.

BACKGROUND

Anemia is defined by either a decreased presence of red blood cells (RBCs) in the blood or a less than normal quantity of hemoglobin. A reduction in the number of RBCs or their function results in a reduced ability of the blood to carry oxygen. This reduction leads to physical symptoms such as fatigue, malaise, weakness, shortness of breath or if extreme, heart palpitations, angina or heart failure symptoms.

There are a multitude of causes for anemia, all resulting in a decrease in functional RBCs and hemoglobin. These causes can be generally grouped into one of three general areas: 1) impaired RBC production; 2) increased RBC destruction; and 3) blood loss. Examples of impaired RBC production include aplastic anemia, iron deficiency, and pernicious anemia. Examples of increased RBC destruction include sickle cell anemia and hereditary spherocytosis. Examples of blood loss include trauma and gynecological or menstrual disturbances.

Anemia is generally monitored via blood tests conducted through a laboratory testing center in which a phlebotomy technician draws a sample of blood and a complete blood count (CBC) conducted. The results of the CBC will show the number of RBCs, hemoglobin level, and often times the size of the RBCs. However, due to the nature of the blood drawing, this type of testing is not appropriate for home testing or self-monitoring purposes.

SUMMARY

Thus, there is need for new type of blood diagnostic tests configured for home-testing or self-monitoring purposes.

In some embodiments, the disclosure may relate to diagnostic kits. In some embodiments, the diagnostic kit may be configured to determine or detect hemoglobin in a sample. In some embodiments, the diagnostic kit may be configured to determine a disease state (e.g., anemic, polycythemia or healthy state) and/or physiological level(s) and/or range(s) of hemoglobin of a test sample. In some embodiments, the kit may include a chamber pre-filled with an indicator solution. The kit may also include a collection device configured to collect a test sample from a subject. In some embodiments, the kit may further include a hemoglobin physiologic level identifier legend, the legend indicating 1) at least one color of the indicator and 2) a physiologic level and/or range of the hemoglobin and/or disease state associated with each color. In some embodiments, the tetramethylbenzidine (TMB) solution may be a 3,3',5,5'-tetramethylbenzidine (TMB) solution. In some embodiments, the kit may further include a puncture device.

In some embodiments, one or more of the collection device, the chamber, the legend, and the puncture device may be separate device. In other embodiments, one or more of the collection device, the chamber pre-filled with an indicator solution, the legend, and the puncture device may be a part of a testing device. In some embodiments, the chamber and the collection device may be separated by a seal (e.g., blister seal) and/or one-way valve.

In some embodiments, the indicator solution may include a reagent solution. The indicator solution may include a tetramethylbenzidine (TMB) solution, the indicator solution being configured to change color, for example, when exposed to a test sample. The reagent solution may include the TMB solution.

In some embodiments, the legend may include at least two colors and the physiologic level and/or range of hemoglobin and/or the disease state associated with each color.

In some embodiments, the indicator solution may further include a buffer solution. The buffer solution may include a mixture of acetic acid and sodium acetate. In some embodiments, the indicator solution may further include a preservative solution. The preservative solution may include a ProClin 300 preservative solution.

In some embodiments, the concentrations of the solutions included in the indicator solution may depend on the level(s) and/or range(s) and/or disease state(s) to be tested. In some embodiments, the at least one color included in the legend may depend on the concentrations.

In some embodiments, the legend may include at least one color and indicate that the color is associated with an anemic state.

In some embodiments, the legend may include more than one color and associated physiologic level(s) and/or range(s) of hemoglobin and/or disease states. In some embodiments, the legend may indicate that at least one color is associated with disease hemoglobin condition/disease state (e.g., anemia or polycythemia) and at least one color is associated with a healthy state. In some embodiments, the legend may be provided in printed form. In some embodiments, the legend may include a plurality of colors and at least one of associated physiologic levels or ranges of hemoglobin and/or disease state.

In some embodiments, the legend may include a color associated with less than 8 g/dL of hemoglobin. The color may be associated with a (severely) anemic state. In other embodiments, the legend may include a color associated with less than 10 g/dL of hemoglobin. The color may be associated with a (mildly) anemic state.

In some embodiments, the legend may include a color associated with less than about 9 g/dL of hemoglobin. The color may be associated with an anemic state. The legend may indicate that a blue color is associated with less than about 9 g/dL of hemoglobin and/or anemic state.

In some embodiments, the legend may include a color associated with about 10-11 g/dL of hemoglobin. The color may be associated with an anemic state. The legend may indicate that a green color and/or a yellow color is associated with about 10-11 g/dL of hemoglobin and/or anemic state.

In some embodiments, the legend may include a color associated with about 12-14 g/dL of hemoglobin. The color may be associated with a healthy state. The legend may indicate that an orange color is associated with about 12-14 g/dL of hemoglobin and/or healthy state.

In some embodiments, the legend may include a color associated with greater than about 14 g/dL of hemoglobin. The color may be associated with a healthy state. The legend may indicate that a red color is associated with greater than about 14 g/dL of hemoglobin and/or a healthy state.

In some embodiments, the puncture device may be a lancet. In some embodiments, the collection device may be made of made of 1 mm thick nitrocellulose "blotting" paper. In some embodiments, the test sample may be whole blood.

In some embodiments, the at least one color may include one or more of the following: blue, green, yellow, orange, and red. In some embodiments, a relationship of the at colors with respect to associated physiologic level or range of hemoglobin may be blue<green<yellow<orange<red.

In some embodiments, the disclosure may relate to a device configured to detect hemoglobin in a sample. In some embodiments, the device may be configured to determine a disease state (e.g., anemic, polycythemia or healthy state) and/or physiological level(s) and/or range(s) of hemoglobin of a test sample. In some embodiments, the device may include a chamber pre-filled with an indicator solution. In some embodiments, the device may further include a puncture device. The device may also include a collection device configured to collect a test sample from a subject. In some embodiments, the device may further include a hemoglobin physiologic level identifier legend, the legend indicating 1) at least one color of the indicator and 2) a physiologic level and/or range of the hemoglobin and/or disease state associated with each color. In some embodiments, the tetramethylbenzidine (TMB) solution may be a 3,3',5,5'-tetramethylbenzidine (TMB) solution. The device may include at least one another chamber. The collection device being disposed in the other chamber.

In some embodiments, the disclosure may relate to a method of determining physiologic levels of hemoglobin in a test sample. The method may include a) adding a test sample to a testing device prefilled with an indicator solution, the indicator solution including a tetramethylbenzidine (TMB) solution, thereby causing the indicator solution to change color; and b) comparing the color of the indicator solution with a legend, the legend including least two color of solutions and associated physiologic level or range of hemoglobin; and c) determining the physiologic level or range of hemoglobin in the test sample based on the color.

In some embodiments, the disclosure may relate to a method of diagnosing a subject suffering from a hemoglobin condition. The method may include a) adding a test sample to a testing device prefilled with an indicator solution, the indicator solution including a tetramethylbenzidine (TMB) solution, thereby causing the indicator solution to change color; and b) comparing the color of the indicator solution with a legend, the legend including least two color of solutions and associated physiologic level or range of hemoglobin; and c) determining whether the subject has anemia based on the color. The hemoglobin condition may include but is not limited anemia and polycythemia.

Additional advantages of the disclosure will be series forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
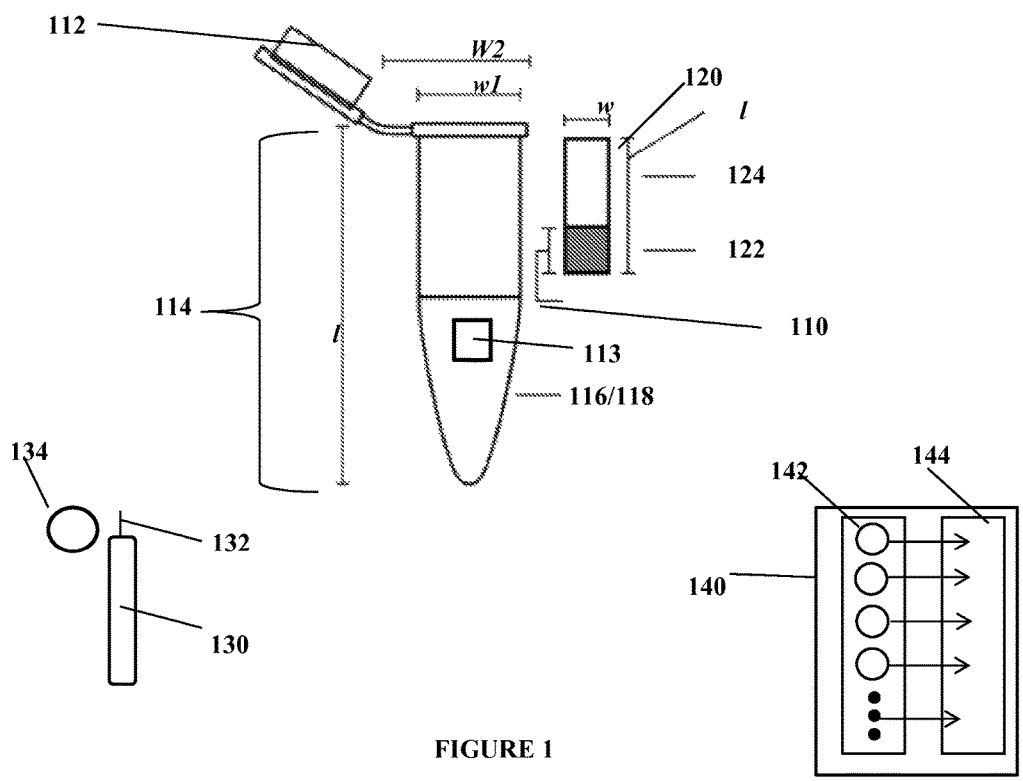
FIG. 1 shows an example of a kit according to embodiments.

The following description, numerous specific details are series forth such as examples of specific components, devices, methods, etc., in order to provide an understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The apparatuses, kits, and methods described herein facilitate rapid, non-invasive determination of physiologic level(s) or range(s) of hemoglobin of a test sample and/or determination of disease state (e.g., anemia and/or polycythemia). The apparatus, kits, and the methods described herein determine the physiologic level(s) and/or range(s) of hemoglobin and/or disease state of a test sample based on a biochemical indicator, according to embodiments. The apparatus, kits, and methods described herein can make a determination of a hemoglobin condition (e.g., anemia or polycythemia) using only a drop of blood, obtained, for example, by a prick of a finger of a user to determine whether they are anemic. The apparatuses, kits, and methods describe herein thereby are configured for home-testing or self-monitoring purposes.

As used herein, the terms "predetermined level" or "predetermined range" refers to generally an assay value or range of values that can be used to assess diagnostic results by comparing the assay or test results against the predetermined level or range. The predetermined level or range may be linked or associated with various clinical parameters (e.g., assessing risk, severity of disease, progression/non-progression/improvement, etc). The present disclosure provides examples of predetermined levels and describes the association of such levels with clinical parameters for exemplary assays as described herein. However, the disclosure is not limited to these predetermined levels and ranges. The "predetermined level" or "predetermined range" may be adjusted according to the application, i.e., the physiologic level(s) and/or range(s) of hemoglobin and/or disease state(s) to be tested and thus the "predetermined level" or "predetermined range" are tunable.

As used herein, "user," "patient," or "subject" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

As used herein, the term "test sample" generally refers to a material being tested for and/or suspected of containing hemoglobin. For example, the material may be a blood substitute. A number of blood substitutes are known in the art. Examples of blood substitutes may include, but are not limited to: recombinant human hemoglobin, crosslinked bovine polyhemoglobin (e.g., Hemopure, Biopure Corporation, Cambridge, Mass.) crosslinked human polyhemoglobin (e.g., PolyHeme®, Northfield Laboratories, Evanston, Ill.), polyethylene glycol-modified hemoglobin (e.g., Hemospan™, Sangart Inc., San Diego, Calif.), polymerized polynitroxyl hemoglobin (e.g., HemoZyme, SynZyme Technologies, LLC, Irvine, Calif.), perfluorocarbon based blood substitutes (See, U.S. Pat. No. 5,374,624; Oxycyte™, Costa Mesa, Calif.), etc. Alternatively, the material may be a biological material being tested for and/or suspected of containing hemoglobin. Biological materials may be derived from any biological source. Examples of biological materials may include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc.

Apparatus & Diagnostic Kits

In some embodiments, the diagnostic kit may include a reservoir or chamber including agent reservoir or configured to hold an indicator solution, indicator solution, and a sample collection device. In some embodiments, the diagnostic kit may include a hemoglobin physiologic level identifier legend (also referred to as "legend"). The diagnostic kit may also include a puncture device. In some embodiments, one or more of these components may be a part of a testing device, separate, or a combination thereof. FIGS. 1 and 6A-8C show examples according to embodiments.

FIG. 1 shows an example of a diagnostic kit (also referred to as a "kit") 100 according to embodiments. In some embodiments, the diagnostic kit 100 may include at least one testing apparatus or device (hereinafter "device") 110. The testing apparatus or device 110 may be any single, use, disposable device, capable of being sterilized and securely closed. In some embodiments, the device 110 may be made of a transparent or partially transparent material. In some embodiments, the device 110 may be made of materials including but not limited to a polymer material.

The device 110 may be of any shape and may be of any dimensions. In some embodiments, the device 110 may have a shape similar to a capillary tube, as shown in FIG. 1. In some embodiments, the device 110 may have a length of about 4.13 cm, a width (w1) of about 1.11 cm (width of device body/housing 114), and a total width (w2) of about 1.90 cm (width of device 110 with the sealing device 112 closed). However, the device 110 shown in FIG. 1 is merely an example and the device 110 is not limited to a centrifuge tube. In other embodiments, the device 110 may have a different shape. For example, the device 110 may have an elongated flush shape, for example, an elongated rectangle, about the size or smaller than the size of a credit-card. In some embodiments, the device 110 may be hinged, like a book. See FIGS. 6A-8C for additional examples of a testing device according to some embodiments.

The device 110 (e.g., the device body/housing 114) may include at least one chamber. In some embodiments, the device 110 may include more than one chamber. In some embodiments, the device 110 may include a first chamber and a second chamber. In additional embodiments, the device 110 may include more than two chambers (e.g., a third chamber). One or more of the chambers may be separated by, for example, a layer that is configured to be broken (e.g., a blister, seal) and/or one-way valve.

In some embodiments, the device 110 may be configured to being opened and securely closed. In some embodiments, the device 110 may include a sealing device (also referred to as "cap") 112. In some embodiments, the sealing device 112 may be attached to a device body (also referred to as "device housing") 114. In other embodiments, the sealing device 112 may be separately disposed. In other embodiments, the device 110 may not include a sealing device.

In some embodiments, the device 110 may include an agent reservoir (also referred to as "chamber") 116 configured to hold an indicator solution 118. The agent reservoir 116 may be disposed in a chamber of the device body 114. In some embodiments, the device 110, for example, the agent reservoir 116 may include or be prefilled with a specific amount of an indicator solution 118.

In some embodiments, the agent reservoir 116 may be disposed at the bottom of the device body 114. In other embodiments, the agent reservoir 116 may include be disposed at other positions on the device body 114. For example, if the device body has an elongated, flat shape, the agent reservoir 116 may be disposed in the center and/or at one side of the device body 114. See FIGS. 6A-8C for additional examples of a testing device according to some embodiments.

In some embodiments, the indicator solution 118 may include a hemoglobin reagent. The indicator may include a tetramethylbenzidine (TMB) solution. In some embodiments, the hemoglobin reagent may include 3,3',5,5'-tetramethylbenzidine (TMB) solution. TMB generally oxidizes to form a blue product. TMB has the following oxidation-reduction chemical reaction:

$$\text{TMB} + \genfrac{}{}{0pt}{}{\text{Hgb}}{\text{H}_2\text{O}_2} \longrightarrow \text{TMB (oxidized)} + \text{H}_2\text{O} \quad [1]$$

In other embodiments, the indicator solution 118 may include additional or different reagent(s).

In some embodiments, the indicator solution 118 may further include a buffer solution. In some embodiments, the buffer solution may correspond to a mixture of acetic acid and sodium acetate, titrated to pH 5.3. In other embodiments, the indicator solution 118 may include additional or different buffer solution(s).

In some embodiments, the indicator solution 118 may further include a preservative solution. In some embodiments, the preservative solution may include but is not limited to ProClin 300 preservative solution. In other embodiments, the indicator solution 118 may include alternative or different preservative solution(s). In further embodiments, the indicator solution 118 may omit a preservative solution. If the indicator solution 118 omits a preservative solution, the device 110 pre-filled with the indicator solution 118 may need to be refrigerated.

The concentrations of the reagent, buffer solution, and/or preservative solution may vary. The concentrations may depend on and/or tailored to the application, i.e., the physiologic level(s) and/or range(s) of hemoglobin and/or disease state(s) to be tested. Varying the concentrations, for example, the relative reagent concentration, may change the resultant color change of the indicator when reacted with a test sample, for example, blood (as discussed in more detail below). The concentrations may also depend on and/or tailored to the subject or population of subjects to be tested, for example, the hemoglobin condition(s).

For example, in some embodiments, the concentrations may be specific to detect mild anemia (hemoglobin level of about 11-12 g/dL), which may be sufficient for screening anemia in the general population. In other embodiments, the concentrations may be specific to detect "moderate" or "severe" anemia, for example, for subjects with chronic anemia due to various diseases. The detection of "mild anemia" may not be useful subjects that know they have anemia. However, it could be useful for them to know if they have "moderate" or "severe" anemia because that would prompt medical intervention. In other embodiments, for example, the indicator solution may have concentrations to detect whether the hemoglobin is less than about 10 g/dL, for example, for chronic anemia patients. In other embodiments, the indicator solution may have concentrations to detect whether the hemoglobin levels are less than about 8 g/dL, for example, for example, to detect subjects that are severely anemic. This may be useful in emerging markets in the global health setting where standard blood counting machines can be cost prohibitive. In other embodiments, the concentrations may be specific to detect polycythemia.

In some embodiments, the device 110 may include an observation region 113. The observation region 113 may be an area of transparent material in which the color change of the indicator solution 118 may be observed. The observation region 113 may have any shape and is not limited the square shape shown. For example, the observation region 113 may have a circular shape. The observation region 113 may be disposed on the device 110 adjacent to the chamber 116 or may be configured to be disposed adjacent to the chamber, for example, when the device is sealed or closed (e.g., a cap). In some embodiments, the observation region 113 may be or may be configured to be on a side of the chamber 116. For example, the observation region 113 may be disposed on a flush top or bottom face of the chamber. See FIGS. 6A-8C for additional examples.

In some embodiments, the kit 100 may include at least one sample collection device (also referred to as "collection device") 120 configured to collect a test sample. The sample collection device 120 may be any device configured to collect a test sample. The sample collection device may include, but, is not limited to, a capillary tube, a porous member (e.g., a test trip), and/or any known sample collection device. For example, see FIGS. 1, 6A, 6B, and 8A-C.

In some embodiments, the sample collection device 120 may be configured to collect or wick about 5 µL of a test sample, for example, whole blood. In some embodiments, the sample collection device 120 may be a porous member similar to a test strip. For example, see FIGS. 1, 7A and 7B. In some embodiments, the sample collection device 120 may be made of 1 mm thick nitrocellulose "blotting" paper, such as the type commonly used for Western blotting. In some embodiments, the sample collection device 120 may have a width (w) of about 0.5 cm and a length (l) of about 2.0 cm.

The collection device 120 is not limited to a strip having these dimensions and may have different dimensions. For example, in some embodiments, the collection device 120 may be a strip having different dimensions, such as dimensions that have a ±5% tolerance. Additionally, the collection device 120 may have a different shape and/or type of collection. For example, see FIGS. 7A and 7B. In some embodiments, the collection device 120, for example, may be similar to a cotton swab and/or capillary tube.

In some embodiments, the collection device 120 may not be separated from the testing device 110 and may be a part of the device 110. In some embodiments the device 110 may be disposed on a receptacle for holding the collection device 120. In some embodiments, the device 110 may include the collection device 120 on a different location. For example, the sealing device 112 may include the collection device 120. For example, the sealing device 112 may include an opening configured to receive the test sample.

In some embodiments, the collection device 120 may be disposed on the housing 114. In some embodiments, the collection device 120 may be disposed adjacent to the agent reservoir 116. See FIGS. 6A-8C for examples. The collection device 120 and the agent reservoir 116, for example, may be separated by a blister seal, one-way valve, as well as other types of seals. In some embodiments, the seal may be broken by shaking and/or a puncture.

In some embodiments, the sample collection device 120 may include at least (first) section 122 configured to collect or receive the test sample. In some embodiments, the sample collection device 120 may include more than one section. In some embodiments, the sample collection device 120 may include a second section 124 configured to be handled by a user. The sections may be disposed on the sample collection device or may be separated.

In some embodiments, a part of the sample collection device 120 may be configured to allow and/or accessible for controlled sample collection or uptake. In some embodiments, the sample collection device 120 may be at least partially coated with a paraffin wax. In some embodiments, only the second section 124 may be covered with paraffin wax. In some embodiments, the sample collection device 120 may be only partially accessible, for example, an opening of the sample collection device.

FIGS. 6A-8C show examples of a testing housing or device in which the collection device and the agent reservoir are disposed on the device housing according to some embodiments. It will be understood the embodiments of the kit, such as the testing device or housing, indicator solution, collection device, puncture device, described with respect to FIGS. 1-3 may also apply to the testing device shown in FIGS. 6A-8C. The devices shown in FIGS. 6A-8C may also be used for other tests (e.g., not limited to hemoglobin tests).

Figure 6A:
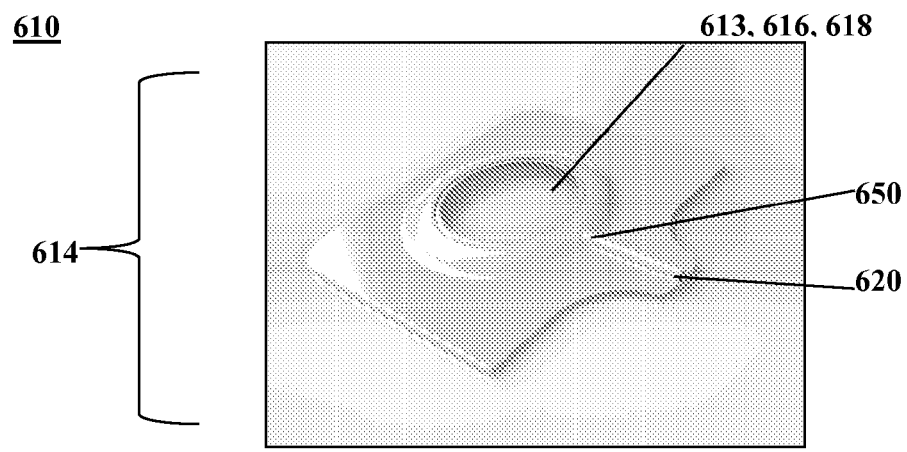
FIGS. 6A and 6B show a perspective view and a top view, respectively, of an example of a testing device according to embodiments.
Figure 6B:
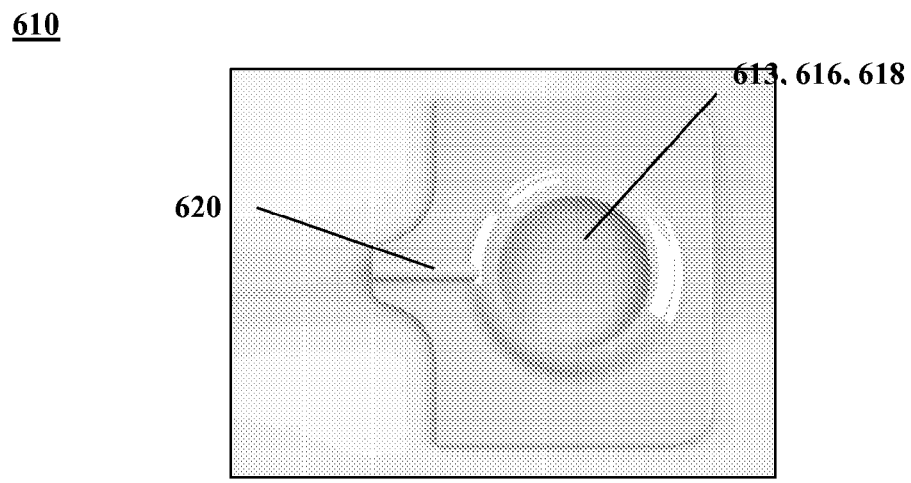

In some embodiments, the testing device may have a substantially flat, rectangular shape. FIGS. 6A-8C show examples of devices according to embodiments. FIGS. 6A and 6B show perspective and top views of a device 610. The device 610 may include a device body (also referred to as "housing") 614. The device 610, housing 614 may have a rectangular flat shape. The device 610 may include an agent reservoir (also referred to as "chamber") 616 configured to hold an indicator solution 618 and/or prefilled with an indicator solution 618 (e.g., the indicator solution described with respect to 118). The device 610 may also include an observation region 613 disposed on at least one side of the agent reservoir 616. The device 610 may also include a collection device 620. The collection device 620 may be configured to communicate with the reservoir. The collection device 620 may be a capillary. The collection device 620 may include more than one section. The housing 614 may include one section. The device 610 may include another body having a complimentary configuration (not shown) including another section. The other body may be configured to initially collect a test sample and deliver the sample, and/or seal the device 620, for example, when the device is shaken. The housing 614 may also include a one-way valve 650 between the device 620 and the reservoir 616.

Figure 7A:
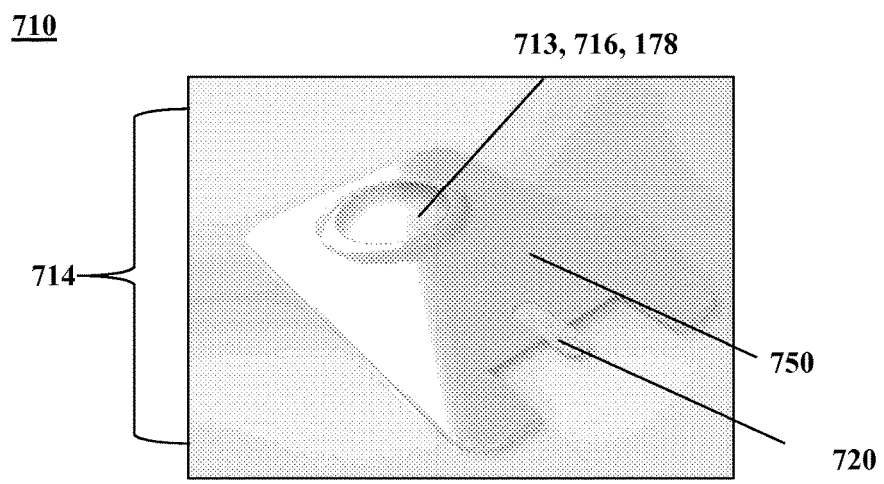
FIGS. 7A and 7B show a perspective view and a top view, respectively, of an example of a testing device according to embodiments.
Figure 7B:
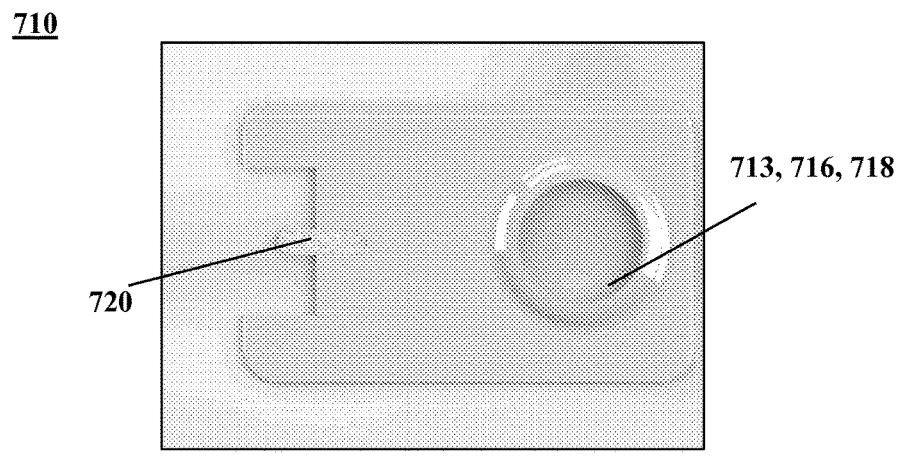

FIGS. 7A and 7B show perspective and top views of a device 710. The device 710 may include a device body (also referred to as "housing") 714. The device 710, housing 714 may have a rectangular flat shape. The device 710 may include an agent reservoir (also referred to as "chamber") 716 configured to hold an indicator solution 718 and/or prefilled with an indicator solution 718 (e.g., the indicator solution described with respect to 118). The device 710 may also include an observation region 713 disposed on at least one side of the agent reservoir 716. The device 710 may also include a collection device 720 disposed on the housing 714. The collection device 720 may be a porous member configured to collect or wick about 5 μL of a test sample. The housing 714 may also include a one-way valve 750 between the collection device 720 and the reservoir 716.

Figure 8A:
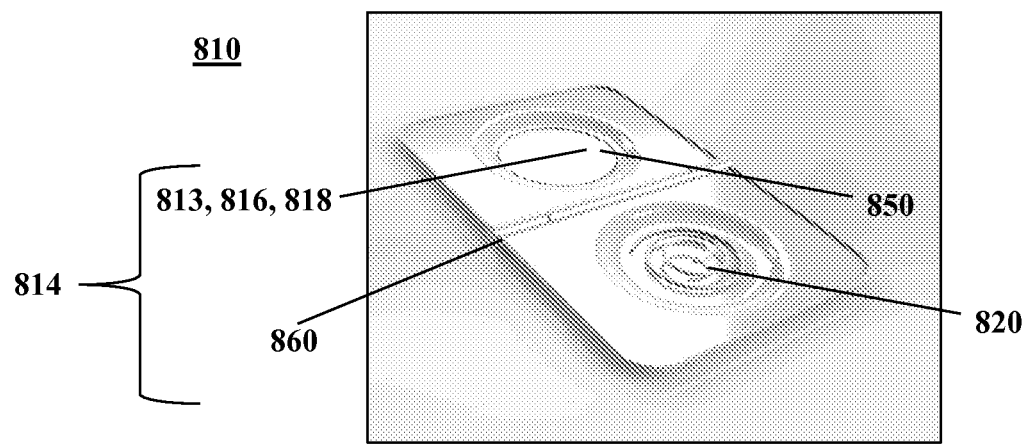
FIGS. 8A-8C show a perspective view of a testing device in expanded state, a different perspective view of the testing device in an expanded state, and the testing device in closed or closed sate, according to embodiments.
Figure 8B:
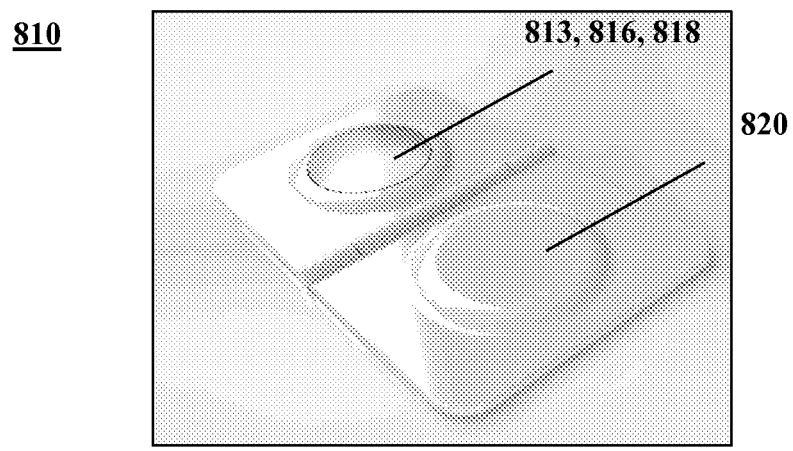
Figure 8C:
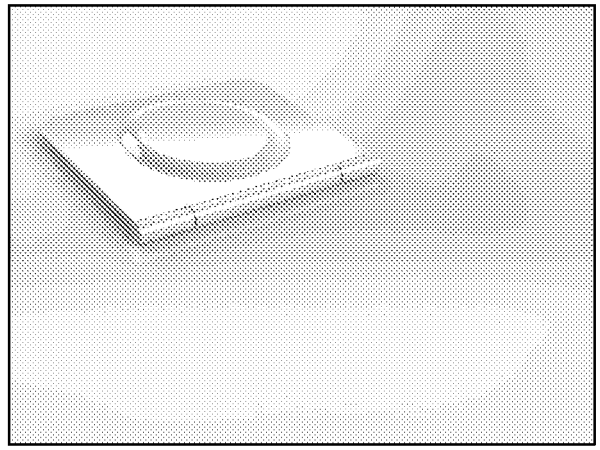

In some embodiments, the device may be configured to seal itself, for example, by being configured to fold or closed upon itself. FIGS. 8A-C show an example of a device according to embodiments. FIGS. 8A and 8B show perspective views of a device 810 in open state or position, and FIG. 8C shows a perspective view of the device 810 in a closed state or position. The device 810 may include a first device body (also referred to as "housing") 814. The device 810 may have a rectangular flat shape, and be separated by a hinge-like device 860. The device 810 may include an agent reservoir (also referred to as "chamber") 816 configured to hold an indicator solution 618 and/or prefilled with an indicator solution 818 (e.g., the indicator solution described with respect to 118). The chamber 816 may be disposed on one side of the device 810. The device 810 may also include an observation region 813 disposed on at least one side of the agent reservoir 816. The agent reservoir may be sealed with a seal 850 (e.g., blister seal). The device 810 may also include a collection device 820 disposed on opposite side of the device 810 (e.g., a cap or the sealing device). The collection device 820 may be a capillary. The collection device 820 may have any shape, e.g., a spiral shape, a u-shaped capillary. The collection device 820 may be configured to collect about 5 μL of a test sample capillary. An adhesive may surround the collection device 820. The collection device 820 may be covered with a cover to maintain sterility. The device 810 may be configured to close (e.g., as shown in FIG. 8C). As the device is closed, the device may be closed and/or sealed, for example, by pressing the adhesive surface surrounding the collection device 820 to the opposite side. The blister seal may then be configured to be broken, for example, by pinching the sides of the device, so that the indicator solution mixes with the test sample.

In some embodiments, the kit may include a puncture device. FIG. 1 shows an example of a puncture device 130. In some embodiments, the puncture device 130 may be any puncture device configured to prick a finger of a user to draw blood and is not limited to the puncture device shown in FIG. 1. For example, the puncture device 130 may be any lancet-type device. In some embodiments, the puncture device 130 may not be separate from the testing device 110 and may be a part of the device 110. In some embodiments, the device 110 may include a receptacle for holding the puncture device 130.

In some embodiments, the puncture device 130 may include a puncture member 132, such as a needle. The puncture device 130 may also include a cap 134. In other embodiments, the kit 100 may omit a puncture device.

In some embodiments, the diagnostic kit 100 may include a hemoglobin physiologic level identifier legend (also referred to as "legend") 140. The legend 140 may include at least one color and associated physiologic level and/or range of hemoglobin and/or disease state. The at least one color may be indicative of the color(s) of the indicator associated with a range and/or physiologic level of hemoglobin and/or disease state. In some embodiments, the at least one color included in the legend may depend on the concentrations of the solutions provided in the provided in the indicator solution. The indicated color and associated level and/or range of hemoglobin and/or disease state may depend on the concentrations of the solutions provided in the indicator solution.

In some embodiments, the legend may include more than one color and associated physiologic level and/or ranges and/or disease state. In some embodiments, the legend may indicate that at least one color is associated with at least one hemoglobin disease state (e.g., anemic disease state and/or polycythemia disease state) and at least one color is associated with a healthy state. In some embodiments, the legend may include a plurality of colors and associated physiologic levels or ranges of hemoglobin and/or disease state.

Figure 2:
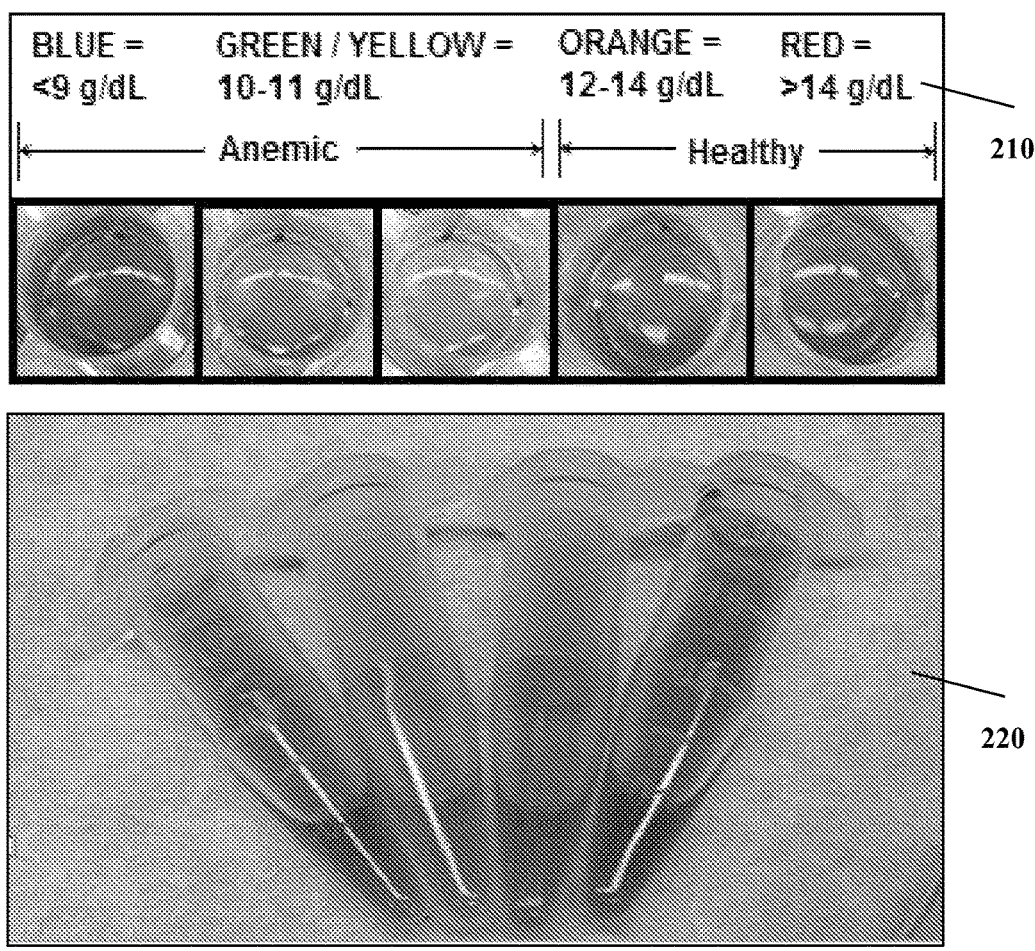
FIG. 2 shows an example of a legend and devices containing colored indicators.

In some embodiments, each color may be associated with a different physiologic level or range of hemoglobin and/or disease state. FIG. 2 shows an example of colored indicators associated with different physiologic ranges of hemoglobin and disease state. FIG. 2 shows an example of a legend 210, and an example of devices 220 containing colored indicator solutions.

It will be understood that the legend is not limited to the colors, levels and/or ranges of hemoglobin and/or disease states shown in FIG. 2. The legend may include more or less colors and the associated levels or ranges and/or disease states. For example, the legend 140 may include a plurality of colors or samples of colors 142 representative of the different colors of the indicator solution and the associated ranges and/or disease states 144. In some embodiments, the legend 140 may include at least one color. In some embodiments, the legend may include at least two different colors. In other embodiments, the legend 140 may include at three colors, four colors, five colors, or more than five colors.

In some embodiments, the colors may include at least one of the following: blue, green, yellow, orange and red. FIG. 2 shows an example of a legend, colors, and associated ranges. It will be understood that the legend is not limited to these ranges and/or colors. For example, the ranges associated with these colors and the colors, themselves, can be tunable and can be adjusted to the chosen concentrations of the reagent, buffer solution, and/or preservative solution. These colors may have the following relationship with respect to the associated physiologic level or range of hemoglobin per g/dL: blue<green<yellow<orange<red. It will be understood that the relationship between these colors and associated physiologic level or range of hemoglobin may be constant. For example, the ranges of hemoglobin level associated with the color(s) may be shifted upward or downward depending on the subject or population of subjects to be tested (e.g., disease state). The relationship between these colors and physiologic level or range of hemoglobin may also not change even if one or more colors are omitted.

For example, in some embodiments, the legend may include a color associated with mild anemia (hemoglobin level of about 11-12 g/dL), which may be sufficient for screening anemia in the general population. In other embodiments, the concentrations may be specific to detect "moderate" or "severe" anemia, for example, for subjects with chronic anemia due to various diseases. The detection of "mild anemia" is not generally useful for them to see a color change at the "mild" level because they already know they have anemia. However, it could be useful for them to know if they have "moderate" or "severe" anemia since that would prompt medical intervention. In other embodiments, for example, the legend may include a color associated with a hemoglobin value less than about 10 g/dL, for example, for chronic anemia patients. In other embodiments, the legend may include a color associated with less than about 8 g/dL, for example, for example, to detect subjects that are severely anemic. This may be useful in emerging markets in the global health setting where standard blood counting machines can be cost prohibitive. In some embodiments, the colors may be associated with higher hemoglobin levels, for example, one or more levels associated with polycythemia.

In some embodiments, the legend may include a color associated with less than 8 g/dL of hemoglobin and/or a (severely) anemic state. In other embodiments, the legend may include a color associated with less than 10 g/dL of hemoglobin and/or a (mildly) anemic state.

In some embodiments, the legend may include a color associated with less than about 9 g/dL of hemoglobin and/or an anemic state. The legend may indicate that a blue color is associated with less than 9 g/dL of hemoglobin and/or anemic state.

In some embodiments, the legend may include a color associated with about 10-11 g/dL of hemoglobin and/or an anemic state. The legend may indicate that a green color and/or a yellow color is associated with about 10-11 g/dL of hemoglobin and/or anemic state.

In some embodiments, the legend may include a color associated with about 12-14 g/dL of hemoglobin and/or a healthy state. The legend may indicate that an orange color is associated with about 12-14 g/dL of hemoglobin and/or healthy state.

In some embodiments, the legend may include a color associated with greater than about 14 g/dL of hemoglobin and/or a healthy state. The legend may indicate that a red color is associated with greater than about 14 g/dL of hemoglobin and/or a healthy state.

In some embodiments, the legend may include a color associated with greater than about 15.5-16 g/dL of hemoglobin and/or a polycythemia state.

In some embodiments, the legend 140 may be in printed form or on CD, DVD, or other format of record media. The legend 140 may be provided as a separate document or instruction manual. In other embodiments, the legend 140 may be integrated into the device 110, a container holding a plurality of collection devices, the testing device, and/or other components of the kit.

In some embodiments, the kit may include one or more instructions for determining physiologic levels of hemoglobin and/or disease state of a subject. Such instructions optionally may be in printed form or on CD, DVD, or other format of record media.

In some embodiments, the component(s) of the diagnostic kit may be sterilized. In some embodiments, the component(s) of each diagnostic kit may be individually packaged for single use. The component(s) of the diagnostic kit may be packaged individually, partially or completely together. In some embodiments, the component(s) of diagnostic kit may be packaged in any airtight, light-resistant material. For example, in some embodiments, the component(s) of diagnostic kit may be packaged in aluminum laminated polyethylene terephthalate (ALPET).

In some embodiments, the diagnostic kit may be sterilized before and/or after the packaging by any method. For example, in some embodiments, after packaging, to ensure package integrity, electron beam sterilization may be conducted.

In some embodiments, the kit may include a plurality of testing devices pre-filled with an indicator solution including a reagent solution. In some embodiments, the testing devices may have the same indicator solution. In other embodiments, at least two devices may differ in the concentration of the reagent solution. In some embodiments, the kit may include at least one legend. In further embodiments, the kit may include at least two legends. In some embodiments, the kit may include a legend for each testing device. In some embodiments, the kit may further include a plurality of collection devices. In further embodiments, the kit may further include a plurality of puncture devices.

Methods

In some embodiments, the disclosure relates to methods of detecting and/or quantifying physiologic levels of hemoglobin in a test sample. The method involves obtaining a test sample, for example, using a collection device. For example, a user may prick their finger with a puncture device, such as puncture device 130, and collect the blood drop with a collection device. The test sample may also be obtained using any routine technique. The method may use the devices and kits according to embodiments and described with respect to FIGS. 1-3 and 6A-8C.

Once the test sample is collected, the sample may be added an indicator solution according to embodiments. For example, the sample via the collection device may be placed into a chamber or reservoir prefilled with an indicator solution. After the sample is placed in the chamber or reservoir, the device including the chamber may be shaken. In some embodiments, the device may need to be closed securely (e.g., closing the cap or closing the device) before the device can be shaken. The device may be shaken for up to about a minute (for example, the device may be shaken about twenty seconds, thirty seconds, forty-five seconds, etc.). The device may also be shaken more or less time.

After the test sample has contacted with the indicator solution, the indicator solution may change color indicating the level of hemoglobin and/or disease state associated with the test sample. The indicator may change color from, for example, to a transparent indicator to a color. The color may change for example, after about a minute. In some embodiments, the color may change after a longer length of time, for example, within about five minutes.

In some embodiments, once the indicator changes color, the range or level of hemoglobin may be determined in the test sample by comparing the color of the indicator to a physiologic level identifier legend, for example, the legend 140. In further embodiments, the subject may be diagnosed with a hemoglobin condition (e.g., anemia or polycythemia) by comparing the color of the comparing the color of the indicator to a physiologic level identifier legend, for example, the legend 140. Once a determination is made that a subject is suffering from a hemoglobin condition, for example, anemia, the subject can be started on treatment with one or more pharmaceutical compositions.

While various embodiments of the disclosure have been described, the description is intended to be exemplary rather than limiting and it will be appeared to those of ordinary skill in the art that may more embodiments and implementations are possible that are within the scope of the disclosure.

Experimental

Quantification of Kit Results can be Achieved Via Spectrophotometric Absorbance Curves.

Figure 3:
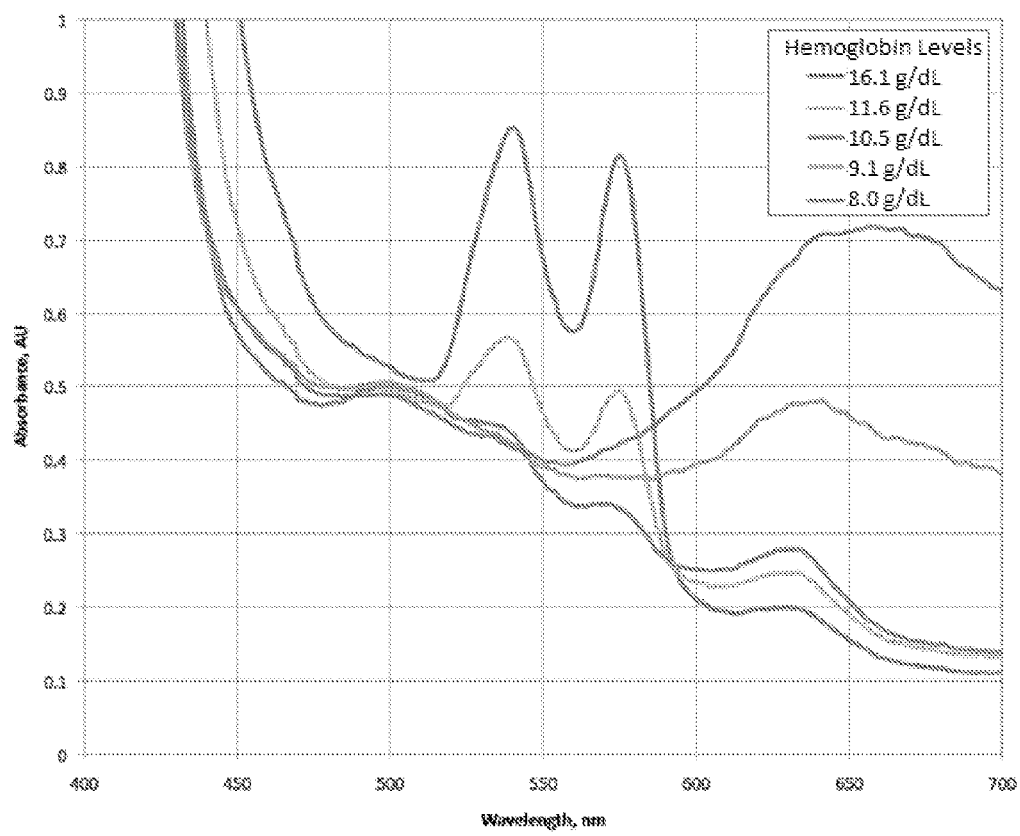
FIG. 3 shows quantification kit results that can be achieved via spectrophotometric absorbance curves.

Assays were performed on patient samples using the kit according to FIG. 1 with different hemoglobin levels: 8, 9.1, 10.5, 11.6, and 16.1 g/dL. Immediately afterwards, absorbance curves were recorded across the visible spectrum, 400-700 nm (blue, green, yellow, orange, red), using a spectrophotometer. As shown in FIG. 3, the final colorimetric absorbance curves for each hemoglobin level are significantly different from each other, thereby demonstrating that the kit according to embodiments is capable of distinguishing anemic blood of varying degrees. The curves indicate especially significant differences in absorbance at 540 nm and 630 nm among the different hemoglobin levels. Therefore, the ratio of absorbances at the 540 nm and 630 nm wavelengths can be used to quantify color and compare results with the kit according to embodiments.

Figure 4:
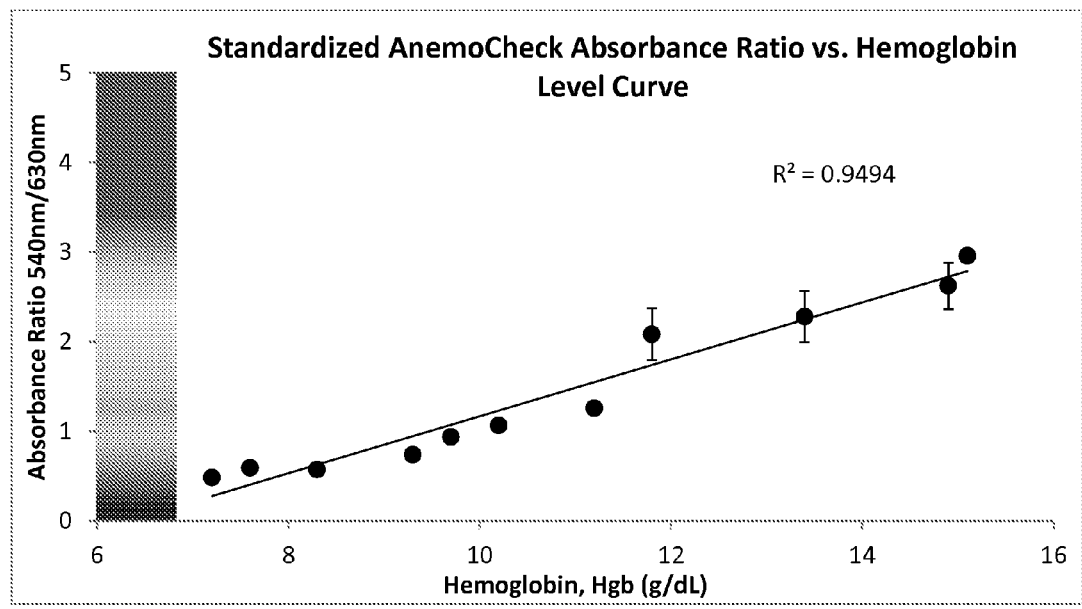
FIG. 4 shows standardized lot Absorbance Ratio vs. Hemoglobin Level curve using a single venous blood sample at various dilutions.

Standardized Kit Absorbance Ratio Vs. Hemoglobin Level Curve using a Single Venous Blood Sample at Various Dilutions A venous blood sample was diluted to different hemoglobin levels using native blood plasma and measured with a hematology analyzer. Each dilution level was then tested with the kit according to FIG. 1 (done in quadruplicate, error bars=standard deviation). Final solution color of the indicator was measured with a visual spectrum plate reader, yielding absorbance values from 400 nm-700 nm. The ratio of absorbance intensities at 540 nm and 630 nm for each patient sample is shown in FIG. 4. This ratio correlates to the final solution color, as indicated with the spectrum to the left.

Figure 5:
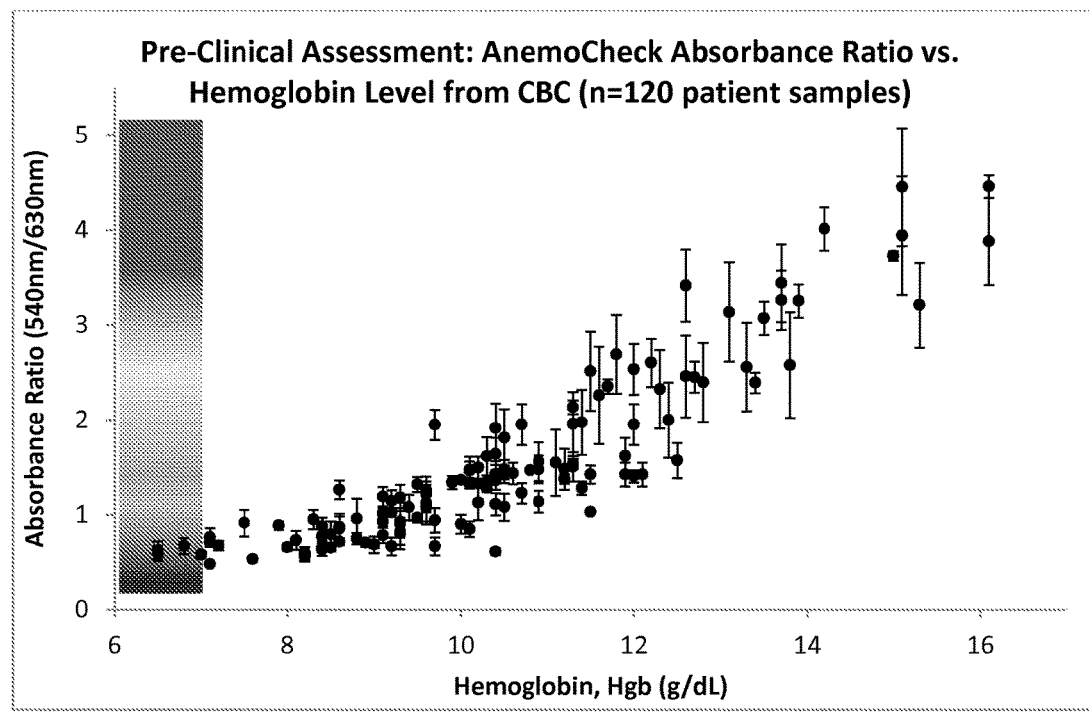
FIG. 5 shows kit absorbance ratio vs. hemoglobin level from CBS of patient venous blood samples in EDTA.

Kit Absorbance Ratio Vs. Hemoglobin Level from CBCs of Patient Venous Blood Samples in EDTA Venous blood samples obtained from hospitalized patients with known hemoglobin values via standard complete blood counts are compared with the kit according to FIG. 1, as shown in FIG. 5 (done in quadruplicate, error bars=standard deviation).

What is claimed is:

1. A method of determining physiologic levels of a hemoglobin in a test sample, the method comprising the steps of:
    a) placing a whole blood sample from a subject into a chamber of a testing device, wherein the chamber is prefilled with an indicator solution, the indicator solution including a tetramethylbenzidine (TMB) solution;
    b) shaking the testing device to cause the indicator solution to directly contact the whole blood sample and change color, the color based on a hemoglobin level in the whole blood sample;
    c) visually comparing the color with a legend, the legend including blue, green, yellow, orange, and red colors and a physiologic level and/or range of hemoglobin associated with each color; and
    d) determining the physiologic level and/or range of hemoglobin in the whole blood sample based on the color, wherein a relationship of the colors with respect to associated physiologic level and/or range of hemoglobin is blue<green<yellow<orange<red.

2. A method of diagnosing a subject suffering from a hemoglobin condition, the method comprising the steps of:
    a) placing a whole blood sample from a subject into a chamber of a testing device, wherein the chamber is prefilled with an indicator solution, the indicator solution including a tetramethylbenzidine (TMB) solution;
    b) shaking the testing device to cause the indicator solution to directly contact the whole blood sample and change color, the color based on a hemoglobin level in the whole blood sample;
    c) visually comparing the color with a legend, the legend including blue, green, yellow, orange, and red colors and a physiologic level and/or range of hemoglobin associated with each color; and
    d) determining whether the subject has the hemoglobin condition based on the color, wherein a relationship of the colors with respect to associated physiologic level and/or range of hemoglobin is blue<green<yellow<orange<red.

3. The method according to claim 1, wherein a blue, green, and/or yellow color indicates an anemic disease state.

4. The method according to claim 1, wherein an orange and/or a red color indicates a healthy state.

* * * * *